US008592219B2

(12) United States Patent
Kange et al.

(10) Patent No.: US 8,592,219 B2
(45) Date of Patent: Nov. 26, 2013

(54) PROTECTING AGENT

(75) Inventors: Rickard Kange, Uppsala (SE); Mats Inganas, Uppsala (SE); Magnus Gustafsson, Solna (SE); Johan Engstrom, Uppsala (SE); Bo Ek, Bjorklinge (SE); Helene Dérand, Taby (SE); Ann-Kristine Honerud, Uppsala (SE)

(73) Assignee: Gyros Patent AB, Uppsala (SE)

( * ) Notice: Subject to any disclaimer, the term of this patent is extended or adjusted under 35 U.S.C. 154(b) by 1126 days.

(21) Appl. No.: 11/038,712

(22) Filed: Jan. 20, 2005

(65) Prior Publication Data

US 2005/0186685 A1    Aug. 25, 2005

(51) Int. Cl.
*G01N 1/00*    (2006.01)
*G01N 1/10*    (2006.01)

(52) U.S. Cl.
USPC ........... 436/174; 436/176; 436/179; 436/180; 436/63; 436/66; 436/68; 436/74; 422/502; 422/503; 422/504

(58) Field of Classification Search
USPC ......... 436/174, 180, 176, 179, 63, 66, 68, 74; 422/502–504
See application file for complete search history.

(56) References Cited

U.S. PATENT DOCUMENTS

| | | | |
|---|---|---|---|
| 4,009,999 A * | 3/1977 | Negersmith .................... 436/53 |
| 4,438,052 A * | 3/1984 | Weder et al. .................... 264/4.6 |
| 4,690,907 A * | 9/1987 | Hibino et al. .................. 436/514 |
| 4,818,686 A | 4/1989 | Kortright et al. |
| 4,988,629 A | 1/1991 | Dopatka et al. |
| 5,215,713 A * | 6/1993 | Steinbiss ........................ 422/61 |
| 5,246,498 A * | 9/1993 | Nitsch et al. .................. 118/429 |
| 5,376,252 A | 12/1994 | Ekstrom |
| 5,605,839 A * | 2/1997 | Simpson et al. ................ 436/89 |
| 5,637,467 A * | 6/1997 | Meltzer ......................... 435/7.9 |
| 5,656,504 A | 8/1997 | Johansson et al. |
| 5,674,700 A * | 10/1997 | Maurel ......................... 435/7.94 |
| 5,688,588 A * | 11/1997 | Cotton et al. .............. 428/305.5 |
| 5,690,841 A | 11/1997 | Elderstig |
| 5,773,488 A | 6/1998 | Allmer |
| 5,858,503 A * | 1/1999 | Everhart et al. .............. 428/131 |
| 5,912,194 A * | 6/1999 | Everhart et al. .............. 442/118 |
| 5,957,167 A | 9/1999 | Feygin |
| 5,962,081 A | 10/1999 | Ohman |
| 5,995,209 A | 11/1999 | Ohman |
| 6,116,297 A | 9/2000 | Feygin |
| 6,126,765 A | 10/2000 | Ohman |

(Continued)

FOREIGN PATENT DOCUMENTS

EP    0 537 828 A1    4/1993
EP    0 328 679 B1    7/1994

(Continued)

OTHER PUBLICATIONS

U.S. Appl. No. 10/169,056, Andersson et al.

(Continued)

*Primary Examiner* — Brian R Gordon

(57) ABSTRACT

A method for transporting in a microfluidic conduit an aliquot of a liquid, possibly containing a substance I, which is dissolved in the liquid and typically exhibits charged groups and/or hydrophobic groups. The method is characterized in that the liquid contains an amphiphilic macromolecular substance.

10 Claims, 3 Drawing Sheets

| Diluent Name and No. | Diluent Composition | | | | | Experimental and/or Predicted Responses | | | | | |
|---|---|---|---|---|---|---|---|---|---|---|---|
| | β-casein (wt%) | NaCl (M) | BSA (%) | Tween 20 (wt%) | Pluronic (wt%) | mTNFa | mIL-6 | hTNFa | hIL-8 | hMCP-1 | hIFNg |
| BSA ref. | - | 0.15 | 1 | - | - | + | + | ++ | 0 | 0 | 0 |
| 1  Low salt diluent with tween | 0.5 | 0.15 | 0.1 | 0.1 | - | ++ | ++ | 0 | + | + | 0 |
| 2  High salt diluent | 0.3 | 0.9 | 0.1 | - | - | 0 | + | ++ | ++ | ++ | + |
| 3  "Tween" | 0.3 | 0.6 | 0.1 | 0.1 | - | + | ++ | 0 | + | ++ | ++ |
| 4  "Pluronic" | 0.2 | 0.5 | 0.1 | - | 0.2 | + | ++ | + | ++ | ++ | ++ |

(56) References Cited

U.S. PATENT DOCUMENTS

| | | | |
|---|---|---|---|
| 6,143,496 A * | 11/2000 | Brown et al. ................. 435/6 |
| 6,144,447 A | 11/2000 | Ohman |
| 6,156,494 A * | 12/2000 | Adams et al. ................. 435/4 |
| 6,171,652 B1 * | 1/2001 | Singh et al. ............... 427/255.6 |
| 6,192,768 B1 | 2/2001 | Wallman |
| 6,203,291 B1 | 3/2001 | Stemme |
| 6,271,195 B1 * | 8/2001 | Hogan, Jr. ................... 514/1 |
| 6,297,061 B1 * | 10/2001 | Wu et al. ................. 436/518 |
| 6,322,682 B1 | 11/2001 | Arvidsson |
| 6,326,083 B1 | 12/2001 | Yang et al. |
| 6,341,182 B1 | 1/2002 | Fitzgerald et al. |
| 6,454,945 B1 * | 9/2002 | Weigl et al. ................. 210/634 |
| 6,454,970 B1 | 9/2002 | Ohman |
| 6,475,364 B1 * | 11/2002 | Dubrow et al. ............. 204/455 |
| 6,498,010 B1 | 12/2002 | Fitzgerald et al. |
| 6,509,059 B2 | 1/2003 | Yang et al. |
| 6,517,778 B1 * | 2/2003 | Kumar et al. ............. 422/82.05 |
| 6,582,662 B1 * | 6/2003 | Kellogg et al. ............... 422/72 |
| 6,613,581 B1 * | 9/2003 | Wada et al. ................. 436/518 |
| 6,620,478 B1 | 9/2003 | Ohman |
| 6,623,972 B2 * | 9/2003 | Malin et al. ................. 436/66 |
| 6,632,656 B1 | 10/2003 | Thomas et al. |
| 6,653,625 B2 | 11/2003 | Andersson |
| 6,709,692 B2 | 3/2004 | Sudor |
| 6,717,136 B2 | 4/2004 | Andersson |
| 6,728,644 B2 | 4/2004 | Bielik |
| 6,759,009 B2 * | 7/2004 | Law ................. 422/73 |
| 6,811,736 B1 | 11/2004 | Ohman |
| 6,812,456 B2 | 11/2004 | Andersson |
| 6,812,457 B2 | 11/2004 | Andersson |
| 6,818,130 B1 * | 11/2004 | Varriale et al. ............. 210/266 |
| 6,858,185 B1 * | 2/2005 | Kopf-Sill et al. ............ 422/100 |
| 6,953,550 B2 * | 10/2005 | Sheppard et al. ............. 422/63 |
| 7,052,915 B2 * | 5/2006 | Aebersold et al. ............ 436/86 |
| 7,179,638 B2 * | 2/2007 | Anderson et al. ......... 435/287.2 |
| 7,264,723 B2 * | 9/2007 | Singh et al. ............. 210/321.6 |
| 7,285,420 B2 * | 10/2007 | Fontaine et al. ............. 436/164 |
| 7,364,897 B2 * | 4/2008 | Heaney et al. ............. 435/287.2 |
| 2002/0005379 A1 * | 1/2002 | Willamson et al. ........ 210/433.1 |
| 2002/0030008 A1 * | 3/2002 | Brunner et al. ............. 210/483 |
| 2002/0072085 A1 * | 6/2002 | Brunner et al. ............. 435/29 |
| 2002/0110900 A1 * | 8/2002 | Jovanovich et al. ....... 435/286.4 |
| 2002/0160518 A1 * | 10/2002 | Hayenga et al. ............. 436/70 |
| 2002/0164820 A1 * | 11/2002 | Brown ................. 436/180 |
| 2003/0015425 A1 * | 1/2003 | Bohm et al. ................. 204/453 |
| 2003/0027354 A1 * | 2/2003 | Geli ................. 436/178 |
| 2003/0044322 A1 | 3/2003 | Andersson |
| 2003/0047823 A1 | 3/2003 | Ohman |
| 2003/0053934 A1 | 3/2003 | Andersson |
| 2003/0054563 A1 | 3/2003 | Ljungstrom |
| 2003/0082075 A1 | 5/2003 | Agren |
| 2003/0094502 A1 | 5/2003 | Andersson |
| 2003/0129360 A1 | 7/2003 | Derand |
| 2003/0143749 A1 * | 7/2003 | Gudmundsson et al. ....... 436/43 |
| 2003/0156763 A1 | 8/2003 | Soderman |
| 2003/0175413 A1 * | 9/2003 | Kahl et al. ................. 427/58 |
| 2003/0211012 A1 | 11/2003 | Bergstrom |
| 2003/0213551 A1 | 11/2003 | Derand |
| 2003/0231312 A1 | 12/2003 | Sjoberg |
| 2004/0014239 A1 * | 1/2004 | Wolk et al. ................. 436/180 |
| 2004/0058408 A1 | 3/2004 | Thomas |
| 2004/0079921 A1 * | 4/2004 | Lynch et al. ............. 252/299.01 |
| 2004/0096867 A1 | 5/2004 | Andersson |
| 2004/0099310 A1 | 5/2004 | Andersson |
| 2004/0115709 A1 | 6/2004 | Morozov et al. |
| 2004/0115721 A1 | 6/2004 | Mao et al. |
| 2004/0120856 A1 | 6/2004 | Andersson |
| 2004/0147045 A1 | 7/2004 | Nelson |
| 2004/0189311 A1 | 9/2004 | Glezer et al. |
| 2004/0202579 A1 | 10/2004 | Larsson et al. |
| 2004/0224425 A1 * | 11/2004 | Gjerde et al. ............. 436/518 |
| 2004/0265172 A1 * | 12/2004 | Pugia et al. ................. 422/58 |
| 2005/0032240 A1 * | 2/2005 | Lee et al. ................. 436/180 |
| 2005/0053642 A1 * | 3/2005 | Ulbricht et al. ............. 424/443 |
| 2005/0244950 A1 * | 11/2005 | Harris et al. ............. 435/287.2 |
| 2005/0277195 A1 * | 12/2005 | Holmquist et al. ............. 436/37 |
| 2006/0000763 A1 * | 1/2006 | Rinker et al. ................. 210/282 |
| 2006/0078998 A1 * | 4/2006 | Puskas et al. ................. 436/64 |
| 2006/0084186 A1 * | 4/2006 | Chaiken et al. ............. 436/518 |
| 2006/0141446 A1 * | 6/2006 | Murphy et al. ................. 435/4 |
| 2007/0017870 A1 * | 1/2007 | Belov et al. ................. 210/656 |
| 2007/0148777 A1 * | 6/2007 | Gilbert et al. ................. 436/56 |
| 2007/0241061 A1 * | 10/2007 | Engstrom et al. ............. 210/749 |
| 2007/0246076 A1 * | 10/2007 | Hafeman et al. ........... 134/22.12 |
| 2008/0057026 A1 * | 3/2008 | Uhrich et al. ............. 424/78.31 |
| 2008/0110820 A1 * | 5/2008 | Knipmeyer et al. .......... 210/474 |

FOREIGN PATENT DOCUMENTS

| | | |
|---|---|---|
| JP | 63016266 A | 1/1988 |
| JP | 6-508690 | 9/1994 |
| JP | 2001-221799 | 8/2001 |
| JP | 2003-114229 | 4/2003 |
| JP | 2004-529336 | 9/2004 |
| JP | 2005-010177 | 1/2005 |
| WO | WO-8901624 | 2/1989 |
| WO | WO-91/16627 | 10/1991 |
| WO | WO-9607909 A1 | 3/1996 |
| WO | WO-9807019 | 2/1998 |
| WO | WO-9853311 | 11/1998 |
| WO | WO-0069560 | 11/2000 |
| WO | WO-0078455 | 12/2000 |
| WO | WO-0079285 | 12/2000 |
| WO | WO-0119518 | 3/2001 |
| WO | WO-0187485 | 11/2001 |
| WO | WO-0187486 | 11/2001 |
| WO | WO-0187487 | 11/2001 |
| WO | WO 03/023360 | 3/2003 |
| WO | WO-2004083108 | 9/2004 |
| WO | WO-2004/083109 | 9/2007 |

OTHER PUBLICATIONS

U.S. Appl. No. 09/958,577, Ulfendahl.
U.S. Appl. No. 10/079,912, Ohman et al.
U.S. Appl. No. 10/867,893, Derand et al.
U.S. Appl. No. 10/182,792, Derand et al.
U.S. Appl. No. 10/129,032, Tormod.
U.S. Appl. No. 10/244,667, Agren.
U.S. Appl. No. 10/450,177, Ohman et al.
U.S. Appl. No. 10/999,532, Ostlin et al.
U.S. Appl. No. 09/869,554, Orlefors et al.
U.S. Appl. No. 10/402,138, Kylberg et al.
U.S. Appl. No. 09/937,533, Larsson et al.
U.S. Appl. No. 10/276,282, Larsson et al.
U.S. Appl. No. 09/830,475, Stjernstrom.
U.S. Appl. No. 10/402,137, Kylberg et al.
U.S. Appl. No. 10/924,151, Tooke et al.
U.S. Appl. No. 11/017,252, Derand et al.
U.S. Appl. No. 09/674,457, Larsson et al.
U.S. Appl. No. 10/111,822, Tooke et al.
U.S. Appl. No. 10/849,321, Fielden et al.
U.S. Appl. No. 10/069,827, Derand et al.
U.S. Appl. No. 10/513,084, Holmquest et al.
U.S. Appl. No. 10/030,297, Derand et al.
U.S. Appl. No. 10/957,452, Ekstrand et al.
U.S. Appl. No. 10/168,942, Tooke et al.
Kricka, L.J., "Human Anti-Animal Antibody Interferences in Immunological Assays," Clinical Chemistry vol. 45, No. 7, 1999, pp. 942-956.
PCT International—Type Search Report, Swedish National Application No. 0500131-8, filed Jan. 17, 2005, Applicant—Gyros AB.
Anderson et al., "A nanoliter-scale nucleic acid processor with parallel architecture," Nat Biotechnol. Apr. 2004; 22(4):435-9. Epub Mar. 14, 2004.
Inganas et al., "Integrated microfluidic compact disc device with potential use in both centralized and point-of-care laboratory settings," Clin Chem. Oct. 2005; 51(10):1985-7.

(56) References Cited

OTHER PUBLICATIONS

Templin et al., "Protein microarrays and multiplexed sandwich immunoassays: what beats the beads?," Comb Chem High Throughput Screen. May 2004;7(3):223-9. Review.PMID: 15134528 [PubMed—indexed for MEDLINE].
Supplemental European Patent Office Communication pursuant to Article 94(3) with extended European search report issued during the prosecution of European Application No. 06700666.8.
Supplemental European Search Report issued during the prosecution of EP Application No. 06700876.
Haes and Van Duyne, A nanoscale optical biosensor: sensitivity and selectivity of an approach based on the localized surface plasmon resonance spectroscopy of triangular silver nanoparticles, *J. Am. Chem. Soc.*, 124:10596-10604, 2002.
Huang et al., "Biotin-derivatized poly (L-lysine)-g-poly(ethylene glycol): a novel polymeric interface for bioaffinity sensing," *Langmuir*, 18:220-230, 2002.

\* cited by examiner

Figure 3

| Diluent Name and No. | Diluent Composition ||||| Experimental and/or Predicted Responses |||||||
|---|---|---|---|---|---|---|---|---|---|---|---|
| | β-casein (wt%) | NaCl (M) | BSA (%) | Tween 20 (wt%) | Pluronic (wt%) | mTNFa | mIL-6 | hTNFa | hIL-8 | hMCP-1 | hIFNg |
| BSA ref. | - | 0.15 | 1 | - | - | + | + | ++ | 0 | 0 | 0 |
| 1 Low salt diluent with tween | 0.5 | 0.15 | 0.1 | 0.1 | - | ++ | ++ | 0 | + | + | 0 |
| 2 High salt diluent | 0.3 | 0.9 | 0.1 | - | - | 0 | + | ++ | ++ | ++ | + |
| 3 "Tween" | 0.3 | 0.6 | 0.1 | 0.1 | - | + | ++ | 0 | + | ++ | ++ |
| 4 "Pluronic" | 0.2 | 0.5 | 0.1 | - | 0.2 | + | ++ | + | ++ | ++ | ++ |

PROTECTING AGENT

CROSS-REFERENCE TO RELATED APPLICATIONS

This application is a Swedish application No. 05001318 filed Jan. 17, 2005, which is incorporated herein in its entirety.

TECHNICAL FIELD

The present invention relates to the transportation of minute liquid aliquots in microfluidic conduits (=transport microconduit) that may be part of a microfluidic device or a device used for the dispensation of such aliquots to microdevices in which a dispensed liquid aliquot is further processed. The transportation is typically part of a predetermined protocol for processing the aliquots. The protocol may be preparative, analytical, synthetic, etc. In a given protocol at least one of the aliquots contains a reactant used in the protocol while other aliquots may be devoid of such reactants, e.g., by merely functioning as washing liquids and/or conditioning liquids and/or diluents for aliquots containing a reactant.

BACKGROUND OF THE INVENTION

The surface to volume ratio increases dramatically when miniaturizing within the nl- and pl-range. It is thus more critical with effective precautions to hinder undesired surface interactions when handling liquid volumes in the lower part of the µl-range such as nl- and pl-volumes compared to larger volumes. Compared to static systems like microtitre wells the problem is far more accentuated for microfluidic systems in which there typically are relatively long transport microconduits, which provide additional contact surfaces that can provide further possibilities for undesired interactions with transported reactants.

Problems with undesired interactions between soluble reactants and functionalized surfaces/reaction areas/reaction zones in microdevices, such as microfluidic devices, have typically been blocked in similar manners as for larger systems. Well known blocking agents are surfactants, inert proteins, such as serum albumin, casein, non-fat dry milk, lactalbumin, gelatin etc., and/or low molecular weight compounds, such as glycine. See for instance U.S. Pat. Nos. 6,341,182 and 6,498,010 (Fitzgerald et al); U.S. Pat. No. 6,613,581 (Wada et al); US 20040115709 (Morozov et al); US 20040115721 (Mao et al); US 20040147045 (Nelson et al); and 20040189311 (Glezer et al). For the similar reasons transport microconduits of microfluidic devices have been modified with coats showing reduced undesired adsorption and denaturation of biologically active molecules (anti-fouling coats/surfaces). See for instance WO 0056810 (Gyros AB), WO 03086960 (Gyros AB), U.S. Pat. No. 6,709,692 (Genset), U.S. Pat. No. 6,236,083 (Caliper), U.S. Pat. No. 6,509,059 (Caliper), etc. In liquid samples containing biological components, there is also a risk that reactants and other components aggregate or otherwise interact in an undesirable manner. These latter problems have typically been counteracted by inclusion of various agents such as detergents and tensides and/or other agents that have surface-active properties.

The inventors have found that many analytes and other reactants used in microfluidic protocols need special precautions in order for a given protocol to reach an acceptable detection limit, precision, recovery etc., and/or to avoid loss of analyte due to underside interactions with inner surfaces. It is attractive to explain at least a part of these difficulties in terms of deficiencies in the surface modification methods and/or the material in which the enclosed microchannel structures are fabricated. The problems encountered typically depend on type of analyte, matrix in which the analyte occurs (serum, plasma, urine, culture supernatant etc.), kind of assay, kind of device including inner surfaces of the device etc. Problematic reactants, in particular analytes, typically are bioorganic molecules that in the worst cases so far found exhibit a biopolymer structure such as protein or polypeptide structure, nucleic acid structure, and/or carry positively and/or negatively charged groups for instance by showing a net positive or net negative charge at the pH used, and/or are relatively hydrophobic. The problems typically are more severe and difficult to overcome the lower the concentration of the analyte is in the undiluted sample, such as a biological fluid. Thus problematic analytes are typically abundant at concentrations $\leq 10^{-6}$ mole/l, such as $\leq 10^{-9}$ mole/l or $\leq 10^{-10}$ mole/l or $\leq 10^{-11}$ mole/l or $\leq 10^{-12}$ mole/l or $\leq 10^{-13}$ mole/l or $\leq 10^{-14}$ mole/l.

The inventors have found that there is a significant risk that an increasing amount of reactant will be lost the longer the analyte sample is retained in the transport microconduit of a dispensation device when dispensing minor aliquots from a larger aliquot to individual microchannel structures of a microfluidic device. This in particular applies to analytical protocols, for instance for aliquots containing the analyte.

BRIEF SUMMARY OF THE INVENTION

An embodiment of the present invention comprises improved compositions, agents and/or methods that generically could be used for improving detection limits and/or precision and/or recovery and/or to prevent loss of analyte in microfluidic protocols of the kind discussed above. The improvement in detection limit for microfluidic assay protocols typically includes measurement of analytes that occur at least down to $10^{-6}$ mole/l, such as down $10^{-9}$ mole/l or down to $10^{-12}$ mole/l or down to $10^{-15}$ mole/l in a native biological fluid. The required detection limit for an analyte is as a rule always $>10^{-25}$ mole/l. The improvement in precision typically means that levels of the analyte concerned is obtained with a coefficient of variation (CV) that is with $\pm 20\%$, such as $\pm 15\%$ or $\pm 10\%$ or $\pm 5\%$. The improvement in recovery typically means that recovery-values $\geq 60\%$, such as $\geq 75\%$ or $\geq 90\%$ or $\geq 95\%$ or essentially around 100% are accomplished.

Another embodiments comprises improved compositions and/or methods that could be used for reducing undesired interactions between constituents of liquids used in microfluidic protocols and/or between such constituents and inner surfaces of the devices used, in particular in transport microconduits. Typical interactions to be reduced include fouling, e.g., undesired adsorption and denaturation caused by contact with inner surfaces.

Still further, another embodiment comprises compositions and methods that enable minimizing matrix effects in the protocols discussed above. More particularly, the present invention can enable use of pre-prepared standard curves and standard values in microfluidic assays protocols, e.g., standard curves/values that are applicable to measured values that are obtained a) at different dates for different analyte samples, and/or b) for two or more different kinds of analyte sample matrixes, e.g., selected from serum, plasma, urine, lachrymal fluid, semen, regurgitated fluid, lymphae, cerebrospinal fluid, cell or tissue homogenates of different origins, cell culture supernatant etc.

The present inventors have found that it can be easier to obtain acceptable results for many of the problematic microfluidic protocols if an exogenous amphiphilic macromolecular substance that typically is capable of forming micelles in water, such as a milk protein that like β-casein and other caseins, is present in one or more of the liquids transported when performing a given protocol in a microfluidic device. Beneficial effects have been obtained both when the transport is taking place within a microfluidic device or in a transport microconduit of a separate device used for the dispensation of liquid to the microfluidic device. The liquids concerned typically contain a reactant, such as an analyte, or are priming, washing or conditioning liquids (WC-liquids). The term "exogenous" means that the substance is not natively present in a biologically derived sample that is used in the protocol to be carried out.

It can be envisaged that similar positive effects are likely to be accomplished if the inner surfaces of the transport microconduits used are precoated with a amphiphilic macromolecular substance exhibiting polypeptide structure.

An embodiment of the present invention comprises a method of transporting an aliquot of liquid (aliquot$_1$/liquid$_1$), comprising steps of providing the aliquot within an upstream end of the microconduit (transport microconduit), and applying a driving force for transporting the aliquot through the microconduit. The aliquot may or may not contain a substance I which is dissolved in the aliquot/liquid.

The characteristic feature is that liquid$_1$/aliquot$_1$ contains one or more of certain protocol enhancers as discussed below and is incorporated herein. For macromolecular enhancers the inner surface of the transport microconduit may be coated with the enhancer before the transport of a liquid aliquot that may or may not contain a protocol enhancer of the types discussed below.

The kind of driving force used may depend on the device in which the transport microconduit is present. Appropriate forces may be created actively, for instance by applying a pressure differential over the microconduit or by passive means. Transport forces may be created electrokinetically e.g., electroendosmosis, or non-electrokinetically e.g. capillary force, inertia force such as centrifugal force, hydrostatic force, forces created by different kinds of pumps etc. See the discussion about dispensation devices and microfluidic devices in this specification.

The liquid is typically aqueous, for instance with water as the main liquid component (>30%, such as >50% (v/v)) possibly in admixture with one or more water-miscible organic liquid components.

In a first subaspect the characteristic feature is that the protocol enhancer is an amphiphilic macromolecular substance that typically is capable of forming micelles (micelle-forming) with itself in water if present above a certain concentration, and/or that inner surfaces of the microconduit are coated with such a macromolecular substance.

In a second subaspect, the characteristic feature is that liquid$_1$ contains an immunoglobulin preparation (Ig) and/or that inner surfaces of the microconduit is coated with such a preparation. The method of transportation according to this subaspect is typically part of an analytical protocol that comprises assaying an analyte in a biological sample by the use of at least one antibody reagent as a reactant in the protocol.

In a third subaspect, the characteristic feature is that liquid$_1$ has an increased concentration of salt (ionic strength) and/or a surfactant that is different from the macromolecular substance of the 1st subaspect. The protocol in this subaspect is typically analytical and comprises assaying an analyte that carries one or more groups that are charged at the pH of liquid$_1$ and/or one or more hydrophobic groups.

Each of the enhancers given above for the 1st-3rd subaspects may be combined with one or more other protocol enhancers. The protocol enhancer of the 1st subaspect is of utmost importance in the invention, but not imperative.

A process protocol utilizing the inventive concept typically comprises processing one or more liquid aliquots through the same transport microconduit or through different transport microconduits that either is/are present in a microchannel structure of a microfluidic device or in a device for dispensation of liquid to a microdevice. At least one of these aliquots has one or more of the characteristic features outlined herein for aliquout$_1$, e.g. contains both substance I in the form of a reactant of the protocol contemplated and/or a protocol enhancer, e.g. according to one or more of the 1st-3rd subaspects, such as the amphiphilic macromolecular substance. If the protocol is analytical (e.g. an assay) the reactant in one or more of the aliquots may be an analyte or a reagent. If an aliquot of liquid contains a reactant, this reactant is typically different from the reactant of other aliquots. One or more of the aliquots transported may have been produced within the microchannel structure but derive from one, two or more aliquots that have been dispensed in one or more earlier steps to the structure, e.g. produced by performing a reaction, a separation, an adsorption, a desorption, a mixing, a diluting etc involving the earlier introduced aliquots. This applies to aliquots containing a reactant as well as to aliquots not containing a reactant.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 3 concludes screening experiments with different combinations of protocol enhancers diluents for diluting five samples containing different analytes (mTNFα, mIL-6, hTNFα, hIL-8, hMCP-1, hIFNγ)

DETAILED DESCRIPTION OF THE INVENTION

I. Definitions

Figure 1:
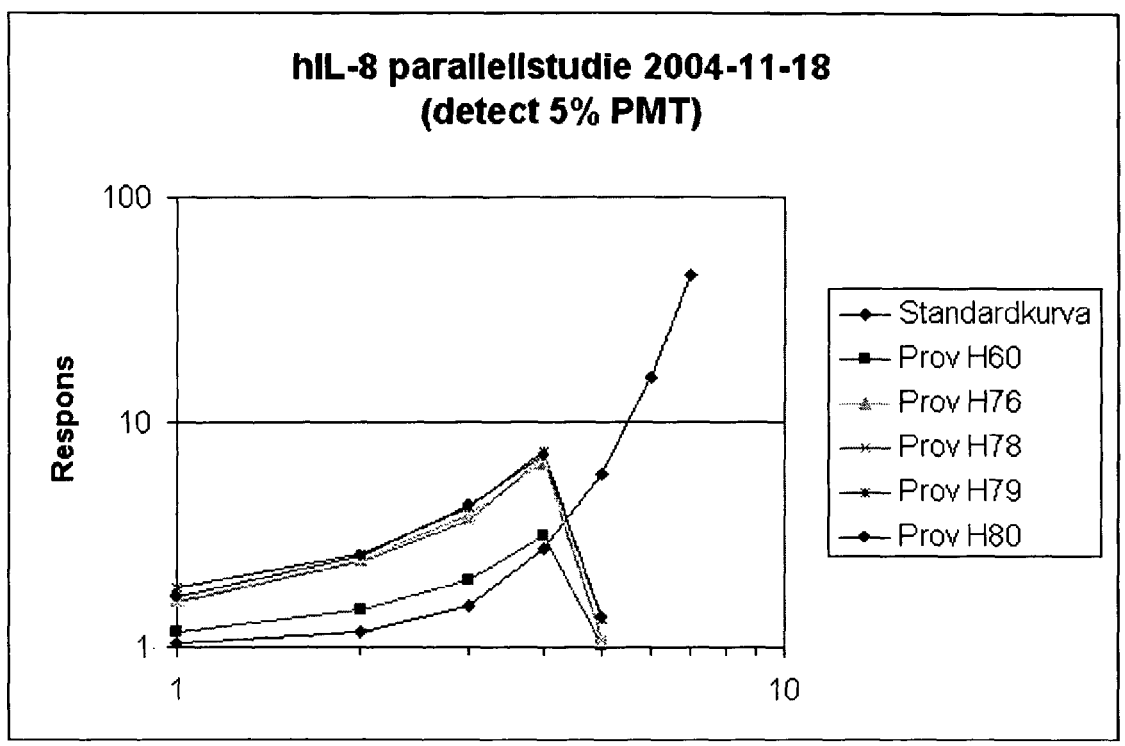
FIG. 1 illustrates the effect of the invention on an hIL-8 assay.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

As used herein, the term "microfluidic device" refers to a device having one or a plurality of microchannel structures which each contains all the functionalities that are required for carrying out those parts of a given microfluidic protocol that are to be carried out in the microfluidic device. Microfluidic protocols and microfluidic devices have been described by among others by Gyros AB/Amersham Pharmacia Biotech AB. See U.S. Pat. No. 6,322,682, U.S. Pat. No. 6,632,656, U.S. Pat. No. 6,717,136, U.S. Pat. No. 6,717,136, U.S. Pat. No. 6,728,644, US 20040120856, US 20040096867, US 20030054563, US 20030094502, US 20030129360, US 20030213551, US 20030044322, US 20030053934, WO 99058245, WO 00025921, WO 00040750, WO 00056808, WO 00062042, WO 010002737, WO 01030995, WO 01047637, WO 01054810, WO 01047638, WO 01046465, WO01085602, WO 02041997, WO 02041998, WO 02075775; WO 0275776, WO 03093802, WO 04050247, WO 04067444, WO 04083109, WO 04083108, WO 04103890, WO 04103891 (U.S. Ser. No. 10/849,321), WO 04106926, PCT/SE04/001424 (U.S. Ser. No. 10/957,852), SE 04008488 (U.S. Ser. No. 60/557,850), SE 04018883 (U.S. Ser. No. 60/588,712), SE 04001814 (U.S. Ser. No. 60/540, 262), SE 0403030-0 (U.S. Ser. No. 60/364,657), etc., each of which is incorporated herein by reference in its entirety.

As used herein, the term "dispensation devices" refer to devices used for dispensation of liquid aliquots to microdevices in which the aliquots are further processed. Microdevices in this context comprise microfluidic devices as well as devices in which no transportation of liquid is taking place, for instance in wells that are arrayed in a plate. Typical dispensation devices include drop dispensers and syringe dispensers, and have been described among others by Gyros AB/Amersham Pharmacia Biotech AB. See US 61972768, WO 01030500, US 20030094502, WO 02075776, WO 02075312, WO 03093802, WO 04083109, WO 04106296, PCT/SE04/001423, SE 0403030-0 and corresponding U.S. provisional Ser. No. 60/364,657", each of which is incorporated herein by reference in its entirety. In other dispensation devices, the outlet of an outlet microconduit (transport microconduit) may be tightly connected to an inlet port of a microfluidic device. Other kinds of dispensers utilize transport microconduits in the form of pins and needles (for instance open tubes) in/on which liquid can be retained by capillarity during transport to a target area on a microdevice (U.S. Pat. No. 5,957,167 and U.S. Pat. No. 6,116,297 (Pharmacopeia) and WO 0119518 (Aclara), each of which is incorporated herein by reference in its entirety.

As used herein, the term "liquid aliquots" refer to an amount of a liquid that is processed in a given protocol and may have the same and/or different volumes and are typically in the μl-range, for example, but not limiting to volumes in the range ≤1,000 μl, such as ≤100 μl or ≤10 μl and includes nanoliter (nl) or picoliter (pl) volumes, i.e. ≤5,000 nl, e.g. ≤1,000 nl or ≤500 nl or ≤5,000 pl.

As used herein, the term "protocol" or "process protocol" is a description of a process and may refer to the order, kind etc of the various steps of the process, such as an experiment. A protocol may include temperature, content of the liquid(s) etc used in the individual steps, for instance reagents, protocol enhancers etc. A protocol may describe an analytical, preparative, synthetic etc process. Analytical processes are often called assays protocol and then describes an assay.

As used herein, the term "protocol enhancer" refers to an exogenous substance that is a non-reactant but can remedy microfluidic protocols or enhance the results of the protocols. This means that the protocol enhancer is not a reactant in the sequence of reactions leading to the product of the process contemplated. Thus a substance/compound that is used for precipitation of disturbing contaminants in an analyte sample is a protocol enhancer even if it is a reactant in the precipitation reaction. Compare that an Ig-preparation according to the 3nd subaspect of the transport embodiment of the invention is used for neutralizing heterophilic antibodies in the sample containing analyte. The protocol enhancer is exogenous in the sense that it is separately added to a liquid containing a reactant of a protocol, e.g. an analyte. In other words a reactant, e.g. an analyte, and a protocol enhancer are not originally present together in the same liquid/sample.

As used herein, the term "dissolved" contemplates that the dissolved entity is a solute and/or suspended in the liquid.

II. Protocol Enhancers

Useful amphiphilic macromolecular substances are typically inherently micelle-forming in water at room temperature (25° C.). This reflects that a suitable substance should have pronounced surface-active properties by comprising hydrophilic and hydrophobic regions in separate parts and/or ends of the molecule. It is believed that the micelle-forming property as such is not important for the invention but merely reflects basic structural features that are important for accomplishing the objects of the invention. The presence of distinct hydrophilic regions and hydrophobic regions in the substance and the macromolecular feature (=a moderate to high molecular weight) are basic criteria for a generically good attachment to a large variety of surfaces including non-wettable as well as wettable surfaces that may or may not be charged.

The exogenous amphiphilic macromolecular substance is typically a non-reactant with respect to the assay reactions, i.e. the reactions leading to formation of the product measured.

In the case a protocol enhancers of the invention is present in a liquid together with a reactant it is preferably in admixture with the reactant before being dispensed to a microdevice, such as a microfluidic device. This in particular applies to analytes.

When present in a liquid together with a reactant or in some other liquid of the type discussed above the concentration of the amphiphilic substance can be below or above the critical micelle concentration (at the temperature of use) (cmc). Micelles of the substance thus may or may not be present. Presence of micelles might have a negative impact on the reliability of the results obtained, in particular if micelles are present together with a reactant, such as an analyte. In solutions used for pre-coating and conditioning it may be beneficial if micelles of the macromolecular substance are included, for instance with the concentration of the amphiphilic macromolecular substance being above cmc. Appropriate concentrations of the amphiphilic substance can typically be found in the interval ≤5%, such as ≤2% or ≤1% or 0.5% and/or ≥0.001%, such as 0.005% or ≥0.01% (w/v-%). The optimal intervals depend on various factors such as kind of reactant, e.g. kind of analyte or reactant reactive with the analyte (e.g. affinity counterpart to the analyte (=anti-An)), kind of amphiphilic substance, concentrations of the analyte and/or of other reactants, other components of the liquids, material exposed on inner surfaces of the device, e.g. plastics including kind of plastics, glass, coatings such as non-ionic hydrophilic polymers, plasma treated surfaces, etc. Experimental testing is required.

The amphiphilic macromolecular substance is thus soluble in the liquid in which it is present and typically has a molecular weight ≥3,000 daltons such as ≥5,000 daltons or ≥10,000 daltons. The molecular weights of natively occurring amphiphilic macromolecular substances are often ≤150,000 daltons, such as ≤100,000 daltons or ≤50,000 daltons. For synthetic variants the upper limit for molecular weight can be considerably higher, e.g. $10^7$ daltons or $5 \times 10^6$ daltons or $10^6$ daltons. These ranges apply to unfragmented forms of the substance. The macromolecular substance is typically a polymer, such as a synthetic, semi-synthetic or native polymer (=biopolymer) and comprises a plurality of the same and/or different monomeric units.

In hydrophilic regions of the macromolecular substance there are typically one or a plurality of at least one of charged and/or non-charged heteroatom-containing groups where the heteroatom typically is oxygen and/or nitrogen. Thus there may be one or a plurality of positively or negatively charged groups, such as quaternary, tertiary, secondary and primary ammonium groups, benzidium groups, phosphate or phosphonate groups, sulphate or sulphonate groups, carboxy groups etc. Some of these groups have a pH-dependent charge in the pH range typically contemplated (pH 1-12, such as 2-11). Typical uncharged hydrophilic groups are alhoholic hydroxy (primary, secondary or tertiary), amido groups, ester groups, repetitive lower alkylene oxide groups, such as repetitive ethylene oxide groups, etc. Lower alkylene in this context primarily means $C_{2-4}$ groups and the term "repetitive" includes that different alkylene oxide groups may be involved.

In hydrophobic regions of the macromolecular substance there typically are one or a plurality of alkyl and/or aryl groups. Corresponding di- and polyvalent groups/structures may also be present. A hydrophobic alkyl group preferably contains one, two, three, four or more $sp^3$-hybridized carbons binding to only hydrogen and carbon and possibly also to fluoro and/or other halogens such as chloro. More specific groups that may be present are selected amongst methyl, ethyl, prop-1-yl, prop-2-yl, 2-methyl-prop-1-yl, but-2-yl, phenyl, benzyl, $CH_3$—S—$CH_2$—, $HSCH_2$—, 1-methyl-prop-1-yl etc, many of which are common in biopolymers that typically exhibit peptide structure or are derivatized to exhibit such groups. The polymer chain may be branched or straight. The chain is typically not cross-linked. If cross-linked it is only slightly without making the polymer as such insoluble in water and/or other liquids.

In certain aspects of the invention, the preferred amphiphilic macromolecular substances have a polypeptide structure, with the preferred ones being found amongst amphiphilic milk proteins, such as amongst the caseins with β-casein being more preferred than others. An amphiphilic macromolecular milk protein may be used together with other milk proteins, such as in defatted milk preparations, possibly in dry form. In this context fragments, aggregates and derivatives of amphiphilic macromolecular substances, typically with micelle-forming properties, are included when a parent form is discussed if not otherwise is apparent from the context. It follows that also micelle-forming polymeric substance other than milk proteins, such as other polypeptides or proteins and synthetic polymers are candidates to be used in the invention. Such candidates may have a high degree of homology with β-casein with respect to the spacing of hydrophobic and hydrophilic monomeric units, such as amino acid residues, if they have polypeptide structure. Examples of potentially useful synthetic polymers are block copolymers comprising hydrophobic regions, for instance with one hydrophobic and one hydrophilic end region, a central hydrophobic region flanked by hydrophilic end regions. This can be illustrated with linear block copolymers, such as the Pluronics that typically have a central polypropyleneoxide region flanked on each end by a polyethyleneoxide region. In principle a useful amphiphilic macromolecular protocol enhancer is non-ionic or ionic, such as anionic, cationic, or zwitterionic.

For analytical protocols utilizing antibody reagents an immunoglobulin preparation (Ig, immunoglobulin) may be included as a protocol enhancer. Since immuno-globulins are macromolecular species the Ig preparation may alternatively be coated on the inner surface of transport microconduits and/or elsewhere throughout a microchannel structure. The Ig-preparation may be of a certain class, such as IgA, IgD, IgE, IgG, and IgM, or subclass. An Ig preparation is included in order to neutralize heterophilic antibodies that may be present together with the analyte in a sample. Compare Kricka L., Clin. Chem. 45 (1999) 942-956. The Ig preparation should thus contain antigenic epitopes that are also present on immunoglobulin from the same species as the species from which an antibody reagent used in the protocol derives. Due to cross-reactivities between species exact species-matching is not required. Ig preparations, if present, should be present in excessive amounts compared to the amount of heterophilic antibodies present in a liquid sample to be mixed or contacted with it. For a liquid aliquot to be transported in the protocol this means that the concentration of this kind of Ig preparation typically is within the interval 0.001-5% such as 0.01-2% or 0.01-1 (w/w-%), preferably in aliquots also containing the analyte. The Ig-preparation may also be present in a liquid aliquot to be transported according to the invention together with a reactant that have affinity for the analyte (anti-An) or some other reactant used. The concentration ranges given also apply if the aliquot/liquid is a coating solution.

The terms "immunoglobulin", "Ig" and "Ig-preparation" referred to above are sometimes named "cold" immunoglobulin since they do not refer antibody preparations that have an antigen/hapten specificity that is relevant for the protocol to be carried out. Substantially all of the antibodies of an Ig-preparation thus are irrelevant unless otherwise suggested by the context.

By securing a sufficiently high salt concentration/ionic strength in a liquid aliquot containing a reactant, such as an analyte, undesired adsorption of the reactant to the inner surface of the transport microconduit and/or other undesired interactions of the reactant can be prevented depending on kind of reactant. This in particular applies if the reactant exhibits charges and/or if an inner surface layer of the transport microconduit contains charges, in particular of the opposite kind as the charge on the reactant. Appropriate salts to be included can be selected from soluble inorganic or organic salts that may be non-buffering at the pH of the liquid transported. Preferred salts can be found amongst soluble salts of group I metals (K, Na etc) with the negative ion typically deriving from a strong acid, i.e. being $SO_4^{2-}$, a halide ion, such as $F^-$, $Cl^-$, etc. Typical the total concentration of salt as defined above should be >0.10 and preferably within the interval 0.15-3 M, such as 0.15-2 M or 0.25-1 M, e.g. in a liquid aliquot containing a reactant, such as an analyte. Appropriate salts should be inert towards the various reactants used and should not create disturbing precipitations. Salt as referred to in this paragraph includes that salt has been added in excess of the salt, if any, that derives from an original liquid sample containing a reactant of the protocol concerned.

Appropriate surfactants for use according to the 3rd subaspect are typically detergents and have a moderate to low molecular weight, such as ≤50,000 daltons, such as ≤20,000 daltons or ≤10,000 daltons or ≤5,000 daltons or ≤3,000 daltons or ≤2,000 daltons. They are selected amongst non-ionic and ionic surfactants where the ionic ones are either anionic, cationic or zwitterionic. They are synthetic (tensides) or native. They are typically micell-forming in the same manner as the macromolecular substance. They exhibit a hydrophobic group and a hydrophilic group selected amongst the same hydrophilic and hydrophobic groups that may be present in the amphiphilic macromolecular substance or in the various kinds of reactants discussed in this specification. Appropriate concentrations of the surfactant of the 3rd subaspect in the aliquot to be transported are typically selected within 0.001-5%, such as 0.01-3% or 0.05-2% (w/v) or 0.01-1% (w/v), e.g. of detergents and tensides, not being originally present together with a reactant, such as an analyte, e.g. in a biological fluid used for obtaining a liquid aliquot to be used in the invention.

The above-mentioned protocol enhancers may be combined with substances that are known to reduce the undesired interactions discussed above. These additional enhancers may be present in the same liquid aliquots as those that contain an enhancer of the $1^{st}$-$3^{rd}$ subaspects. Alternatively they may be introduced in one or more separate aliquots that subsequently may or may not be mixed with an aliquot containing an enhancer of $1^{st}$-$3^{rd}$ subaspect. The concentration of this kind of additional enhancer in a liquid aliquot to be transported in accordance with the invention is typically in the interval 0.001-5%, such 0.01-3% (w/v). A typical such additional enhancer is separately added serum albumin.

III. Reactants

The most significant advantages of the invention are believed to occur when there is a high risk for undesired interactions between a reactant and an inner surface of a transport microconduit. Our experiments so far suggest that the risk for this kind of interactions is highest if the reactant exhibits one or a plurality of groups selected amongst hydrophobic groups and charged groups. A hydrophobic group typically exhibits an aromatic group and/or a cyclic, branched or straight alkyl or alkylene group. Aromatic groups may be illustrated with phenyl and benzyl groups in substituted or unsubstituted forms. Alkyl or alkylene groups may comprise hydrocarbon chains containing one, two, three or more $sp^3$-hybridised carbon atoms, such as in methyl, ethyl, prop-1-yl, prop-2-yl, 2-methyl-prop-1-yl, but-2-yl, phenyl, benzyl, $CH_3$—S—$CH_2$—, $HSCH_2$—, 1-methyl-prop-1-yl etc. As a rule carbon chains in bioorganic molecules have less than 30 carbon atoms. Charged groups are positively and/or negatively charged and include that a reactant has both kinds of groups and a net positive charge, a net negative charge, or a net zero charge. The net charge of the reactant or of a group may be pH-dependent, e.g. the reactant may be zwitterionic, such as an ampholyte with an isoelectric point (pI). These kinds of groups/reactants may potentially interact with inner surfaces that expose hydrophobic groups or groups that have the opposite charge compared to a charged group on a reactant. Interaction may also occur if the charged group of the inner surface is present within a layer below an inner surface, for instance within deficient coating layers, such as in so-called pin-holes, or within a surface layer of the material in which the microchannel structure has been fabricated.

The reactants concerned may be illustrated with analytes, reagents/reactants exhibiting a detectable group, reagents/reactants exhibiting an immobilizing group or tag, etc and are typically bioorganic compounds. Reactants that are bioorganic compounds and exhibit hydrophobic groups may be found amongst proteins and polypeptides, glycolipids and lipoproteins, lipids such as many steroids, fatty acids and fatty acid derivatives such as esters including glycerides, and higher bio-alcohols (with five or more carbon atoms) and their derivatives. Reactants that are bioorganic compounds and/or exhibit charged groups are primarily found amongst proteins including other substances exhibiting peptide structure, and nucleic acids including other substances exhibiting nucleotide structure.

A bioorganic reactant that contains a polypeptide structure typically also contains a) one or more positively charged or chargeable groups, c) one or more negatively charged or chargeable groups and/or b) one or more hydrophobic groups. These kinds of groups are represented by the presence of the following amino acid residues:
(a) N-terminal amino acid and/or basic amino acid residues, such as lysine etc,
(b) C-terminal amino acid and/or acidic amino acid residues, such as aspartic acid, glutamic acid etc, and
(c) amino acids having a hydropathy index larger than zero (Kyte et al., J. Mol. Biol. 157 (1982) 105-132).

Hydrophobic amino acids (hydropathy index in brackets) are: alanine (1.8), cysteine (1.5), leucine (3.8), isoleucine (4.5), methionine (1.9), phenylalanine (2.8) and valine (4.2).

The risk and magnitude of the undesired interactions with inner surfaces many times will be dependent on the conditions provided by the liquid in which a reactant is transported and/or incubated, for instance pH and/or ionic strength (salt concentration) and/or presence of surfactants. In relation to the pH normally contemplated (pH=7.4±0.5) for the liquids in which bioorganic reactions are carried out and/or bioorganic reactants are transported the risk may vary with respect to the actual charge on the reactant. The inventors have for instance found that an amfolyte reactant, for instance, that has a pI larger than pH −1, such as pH, of the aliquot in which it is transported may benefit more than an amfolyte reactant for which pI is less than this pH (plastic $O_2$-plasma hydrophilized surface coated with non-ionic hydrophilic polymer by electrostatic interaction). A positively charged or a more acidified form of a pH-dependent reactant may thus benefit more than a less acidified form, e.g. a basic polypeptide analyte may benefit more than an acidic polypeptide analyte. It is not unlikely that further investigations will show that benefits may also be accomplished for negatively charged reactants, for instance zwitterionic reactants, such as amfolyte reactants that have pI<pH+1, such as <pH, of the aliquot in which it is transported, in particular if microconduits that have inner surfaces comprising positively charged groups are used.

For reactants exhibiting a polypeptide structure the risk for poor performance of a protocol many times also will depend on the type, number and positions of hydrophobic amino acids in the polypeptide structure. The mean hydropathy index for all amino acid residues of a polypeptide structure of a reactant may thus be considered as a measure of these risks, typically with the proviso that the reactant as such exhibits at least one, two, three, four, five or more hydrophobic amino acid residue ("mean hydropathy index"=GRAVY value, (Kyte et al., J. Mol. Biol. 157 (1982) 105-132). Thus it may be beneficial to include the concept of the present invention for the transport of a reactant that has a mean hydropathy index $\geq -0.5$, such as $\geq -0.1 \geq 0$ or $\geq 0.1$ or $\geq 0.2$ or $\geq 0.3$ or $\geq 0.4$. Due to the complexity of polypeptide/protein structure it may many times be better to apply these mean hydropathy ranges to one or more parts of the sequence of the polypeptide structure of a reactant to find reactants that may benefit from the invention. In this context a part sequence comprises from 2, 3, 4, 5, 6 and more consecutive amino acid residues and/or between 1-99%, such as 2-99% or 4-50% or 4-25% or 4-10% or 1-6% of the total number of amino acid residues in the full length sequence. Reactants comprising 1, 2, 3, 4, 5, 6, 7 or more consecutive hydrophobic amino acid residues typically represent reactants that may benefit from one or more of the subaspects of the instant invention.

What have been said above under the heading "Various forms of reactants" in particular relates to reactants that are analytes.

IV. Transport Microconduits

As already indicated elsewhere in this specification transport microconduits are primarily present in: a) dispensation devices, and b) microchannel structures of microfluidic devices.

In dispensation devices a transport microconduit typically comprises a dispensation orifice and thus primarily comprises the outlet part of the liquid transportation system of a dispensation device, i.e. the part from which a liquid leaves the device for a target area of a microdevice. The dispensation device may be a drop-dispenser, plunge driven dispenser (e.g. syringe) or based on other pump mechanisms as is well known in the field. Other kinds of dispensers use transport microconduits in the form of pins or needles to which the liquid aliquot is retained by surface forces, e.g. capillary forces, during the transport. In other words the term "transport microconduit" in the context of dispensation is generic and refers more to transport to a microdevice than transport through a microconduit. The microdevice may be a plate containing a number of wells (microtitre plate), a microfluidic device comprising one or more microchannel structures, etc. The liquid transferred to the microdevice is further processed in the wells, microchannel structures etc.

The greatest advantages are obtained with dispensers in which a larger liquid aliquot is first collected in the transport microconduit and then dispensed in minor aliquots in sequence to different target areas of one or more microdevices.

The transport microconduits of dispensation devices may be fabricated in glass, metal, plastics, ceramics etc. The inner surfaces may be pre-treated as is well-known in the field for liquid transportation systems, i.e. made wettable/hydrophilic and/or equipped with a surface with lowered fouling activity.

In its most general meaning (meaning 1), the term "transport microconduit" in a microfluidic device/microchannel structure contemplates all parts of the microchannel structure through which liquid shall pass except those cavities/microconduits in which heterogeneous reactions of a protocol are to take place and typically also waste chambers/reservoirs (if present) (heterogeneous reaction=a reaction between a dissolved reactant and a solid phase bound reactant). The term "transport microconduit" in the context of the invention shall refer to meaning 1 if not otherwise being clear from the context.

In a more restrictive meaning (meaning 2), reaction microcavities/microconduits in which other kinds of reactions are excluded from being transport microconduits. Typical such other reactions are homogeneous reactions of the protocol, i.e. reactions between reactants in dissolved form.

In a still more restrictive meaning (meaning 3), transport microconduits are microconduits that are only used for transport of liquid aliquots that may or may not contain reactants. In other words a "transport microconduit" in the third meaning has the sole function of transporting liquid between functionalities, such as inlet openings, volume-definition units, valves, vents, mixing units, liquid routing units, units for particle separation from liquids, units for removal of contaminants and disturbing substances, reaction units, detection units etc.

V. Microfluidic Devices

A microfluidic device comprises one, two or more microchannel structures each of which is intended for carrying out a desired protocol by transporting and processing one or more aliquots of liquid. The number of microchannel structures/device is typically $\geq 10$, e.g. $\geq 25$ or $\geq 90$ or $\geq 180$ or $\geq 270$ or $\geq 360$.

Each of the microchannel structures contains one or more cavities and/or conduits that have a cross-sectional dimension that is $\leq 10^3$ μm, preferably $\leq 5 \times 10^2$ μm, such as $\leq 10^2$ μm. The nl-range has an upper limit of 5,000 nl. In most cases it relates to volumes 1,000 nl, such as $\leq 500$ nl or $\leq 100$ nl.

Each of the microchannel structures typically comprises one, two, three or more functional parts selected among: (a) inlet arrangements comprising for instance an inlet port/inlet opening, possibly together with a volume-metering unit, b) microconduits for liquid transport (meaning 3 above), c) reaction microcavities; d) mixing microcavities; e) units for separating particulate matters from liquids (may be present in the inlet arrangement), f) units for separating dissolved or suspended components in the sample from each other, for instance by capillary electrophoresis, chromatography and the like; g) detection microcavities; h) waste conduits/microcavities; i) valves; j) vents to ambient atmosphere; etc. A functional part may have one or more functionalities, e.g. a reaction microcavity and a detection microcavity may coincide. Various kinds of functional units in microfluidic devices have been described by Gyros AB/Amersham Pharmacia Biotech AB: WO 9955827, WO 9958245, WO 02074438, WO 0275312, WO 03018198, WO 03024598, WO 04050247, and by Tecan/Gamera Biosciences: WO 0187487, WO 0187486, WO 0079285, WO 0078455, WO 0069560, WO 9807019, WO 9853311, each of which is incorporated herein by reference in its entirety.

Different principles may be utilized for transporting the liquid within the microfluidic device/microchannel structures between two or more of the functional parts described above. Inertia force may be used, for instance by spinning the disc as discussed in the subsequent paragraph. Other useful forces are capillary forces, electrokinetic forces, non-electrokinetic forces such as capillary forces, hydrostatic pressure etc.

The microfluidic device typically is in the form of a disc. The preferred formats have an axis of symmetry ($C_n$) that is perpendicular to the disc plane, where n is an integer 2, 3, 4 or 5, preferably $\infty$ ($C_\infty$). In other words the disc may be rectangular, such as in the form of a square, or have other polygonal forms. It may also be circular ($C_\infty$). Once the proper disc format has been selected centrifugal force may be used for driving liquid flow, e.g. by spinning the device around a spin axis that typically is perpendicular or parallel to the disc plane. In the most obvious variants at the priority date, the spin axis coincides with the above-mentioned axis of symmetry. See the patent publications discussed above in the name of Gyros AB and Gamera Biosciences/Tecan.

For preferred centrifugal-based variants, each microchannel structure comprises an upstream section that is at a shorter radial distance than a downstream section relative to the spin axis.

The preferred devices are typically disc-shaped with sizes and forms similar to the conventional CD-format, e.g. sizes that corresponds CD-radii that are the interval 10%-300% of the conventional CD-radii.

Microchannels/microcavities of a microfluidic device may be manufactured from an essentially planar substrate surface that exhibits the channels/cavities in uncovered form that in a subsequent step are covered by another essentially planar substrate (lid). See WO 9116966 (Pharmacia Biotech AB), WO 0154810 (Gyros AB), and WO 03055790 (Gyros AB). The material of the substrates may be selected among various kinds of inorganic and organic material, for instance polymeric material, such as plastics.

For aqueous liquids an essential part of the inner surfaces of the microchannel structures should have water contact angles ≤90°, such as ≤60° or ≤40° or ≤30° or ≤20° at the temperature of use or 25° C. At least two or three of the inner walls enclosing the channels should comply with this range. Surfaces in passive valves, anti-wicking means etc are excluded from these general rules. Surfaces made in plastics typically need to be hydrophilized. Useful hydrophilization protocols are for instance given in WO 9529203 (Pharmacia Biotech AB), WO 9800709 (Pharmacia Biotech AB, WO 0146637 (Gyros AB), WO 0056808 (Gyros AB) and WO 03086960 (Gyros AB) etc.

Parts of a microchannel structure that are used for liquid transportation or otherwise intended to be in contact with an aqueous liquid are preferably hydrophilic. By this is meant that the wettability of inner surfaces of such a part supports filling the part with liquid by capillarity (self suction) provided a front of the liquid has passed the entrance of the part, e.g. passed a valve function at the entrance.

Non-wettable surface breaks (water contact angles ≥90°) may be introduced at predetermined positions in the inner walls of the microchannel structures before covering the uncovered microchannel structures (WO 9958245, Amersham Pharmacia Biotech AB) and WO 0185602, Åmic AB & Gyros AB, each of which is incorporated herein by reference). For aqueous liquids this means hydrophobic surface breaks. Surface breaks may be used for controlling the liquid flow within the structures, e.g. in anti-wicking, passive valves, directing liquids etc.

It can be envisaged that a microchannel structure comprising at least one fluidic function based on surface tension such as in capillary valves, anti-wicking means, liquid-directing etc might be simpler to deal with if the macromolecular protocol enhancer is present in dissolved form than in pre-coated form, e.g. the amphiphilic macromolecular substance and/or the Ig-preparation. This concern in particular applies to structures in which these functionalities are based on hydrophobic/non-wettable surface breaks in otherwise hydrophilic microconduits.

A reaction microcavity may comprise a solid phase typically exposing a solid phase bound reactant, such as a reactant that is used in steps leading to formation of the final product of the protocol. Alternatively the solid phase may expose a reactant for removing contaminants and/or disturbing substances that are present in a liquid aliquot passing the solid phase/reaction microcavity.

The solid phase may be the inner walls of the reaction microcavity or a porous bed retained in the reaction microcavity. A porous bed is typically a) a porous monolith, or b) a population of porous or non-porous particles that are packed to a porous bed.

The material in the porous bed, e.g. the particles, is typically polymeric, for instance a synthetic polymer or a biopolymer. The particles and other forms of solid phases are typically hydrophilic in the case the liquid flow is aqueous. In this context hydrophilic encompasses that a porous solid phase, e.g. a packed bead, will be penetrated by water by self-suction. The term also indicates that the surfaces of the particles shall expose a plurality of polar functional groups in which there is a heteroatom selected amongst oxygen, sulphur, and nitrogen. A hydrophobic particle or porous monolith may be hydrophilized, for instance by introducing hydrophilic groups. The coating and hydrophilization technique may be similar to the technique presented in WO 9529203 (Pharmacia Biotech AB), WO 9800709 (Pharmacia Biotech AB, Arvidsson & Ekstrom), WO 0146637 (Gyros AB), WO 0056808 (Gyros AB) and WO 03086960 (Gyros AB), each of which is incorporated herein by reference.

The techniques for immobilization of an reactant to a solid phase may be selected amongst those that are commonly known in the field. Immobilization may thus be via covalent bonds, affinity bonds, physical adsorption (mainly hydrophobic interaction) etc. Examples of biospecific affinity bonds that can be used are bonds a) between streptavidin and a biotinylated affinity reactant, b) between high affinity antibody and a haptenylated affinity reactant etc, and vice versa.

VI. Protocols

As indicated above the liquid transport is typically part of a protocol in which one or more aliquots of liquid are processed within a microdevice, such as a microfluidic device. At least one of the aliquots contains a reactant of the protocol. The protocol may be analytical, preparative, synthetic etc. In principle any kind of synthetic or preparative protocol carried out in a microdevice means that the results are analyzed to find out something about the actual reactions carried out, about the reactants involved, in other words most preparative and synthetic protocols are part of an analytical protocol.

For analytical protocol (assays) the general goal is typically to characterize certain aspects of one or more of the reactions carried out in a protocol. This characterization may relate to learning about one or more molecular features of a reactant (=analyte). Thus one goal may be to find the amount/concentration/activity of an analyte. Another goal may be to learn about reactivity, identity, structure and other features of a reactant (=analyte). In its broadest sense analytical protocols also comprises to study how various reaction conditions/variables such as concentration of a reactant, pH, ionic strength, presence of detergents, type of salts, temperature, presence of various components etc interfere with the result of a reaction protocol. This latter kind of analytical protocols typically comprises comparative studies in which one or more reaction conditions are changed. For these protocols the term "analyte" means the variable(s) that is(are) changed between the comparative experiments.

The typical protocols are applicable to biological science and/or chemistry including medicine, biochemistry, molecular biology, environmental science, diagnostics, inorganic, organic and/or analytical etc chemistry etc. A typical protocol utilizes a bioorganic reactant, e.g. the analyte, while one or more of the other reactants may be inorganic, such as a metal ion or an inorganic anion. In the context of the invention synthetic organic compounds mimicking a bioorganic compound/reactant are also bioorganic.

Illustrative examples of analytes are a) hormones, such as peptide hormones and steroid hormones, b) hormone receptors, c) growth factors, d) components of enzymatic systems, such as enzymes, enzyme substrates, cofactors, coenzymes, cosubstrates etc, e) immune modulators such as cytokines, chemokines including interferons and interleukins, inflammatory mediators, such as ECP, MPO etc, g) antigens and haptens, h) drugs, i) immunoglobulins such as immunoglobulin as such and its subclasses, j) blood clotting factors, k) complement factors, l) tissue, m) microorganisms such as bacteria, mould, fungi, viruses, prions, etc, n) occupational health molecular indicators, o) toxins, p) nucleic acids and other compounds exhibiting nucleotide structure, etc.

Typical protocols (assays) are ligand-receptor assays, catalytic assays, cell-based assays etc. Included are also sample preparation for analyses outside the microdevice, for instance by MS (U.S. Pat. No. 6,812,457 and U.S. Pat. No. 6,812,456 (Gyros AB)).

A. Receptor-Ligand Assays

This kind of protocols comprises a step in which an affinity complex comprising the analyte and an affinity counterpart to the analyte (anti-An) is formed. By proper selection of reaction conditions the amount of (a) complex formed, and/or (b) uncomplexed analyte, and/or (c) uncomplexed anti-An is/are correlated with the starting amount of analyte, e.g. the concentration/amount/activity of the analyte in a fluid from which the analyte derives, e.g. a biological fluid. The measurement of (a), (b) or (c) is often facilitated by the use of an affinity reactant, e.g. anti-An, which comprises a detectable group (detectable reactant), such as a label, and is capable of forming an affinity complex that contains the appropriate one of entities (a)-(c).

Receptor-ligand assays can be divided in two main groups 1) heterogeneous assays and 2) homogeneous assays. A heterogeneous assays comprises a separation step before the measurement is taking place, i.e. the affinity complex is separated from the analyte and/or from anti-An not incorporated into the complex, or the affinity complex containing the detectable reactant is separated from the portion of detectable reactant that is not incorporated into this complex.

Separation is facilitated by the use of an immobilized or immobilizable form of anti-An or an analogue to the analyte (An-analogue). In a homogeneous assay this kind of separation step is not included. In stead one makes use of an affinity reactant that exhibits a detectable group for which the feature to be measured changes as a consequence of affinity complex formation. The inventive concept can be applied to both heterogeneous and homogeneous receptor-ligand assays.

Receptor-ligand assays can also be divided into: 1) competitive assays, and 2) non-competitive assays.

In competitive assays an analyte analogue (An-analogue) is allowed to compete with or inhibit the binding of an analyte to anti-An. Anti-An is typically present in limiting amounts. Competitive assays also include so-called displacement assays which typically comprises a first step in which a limiting amount of anti-An is saturated with An-analogue whereafter the analyte is allowed to displace complex-bound An-analogue. Competitive assays may be homogeneous or heterogeneous. Typical analytes that are used in competitive assays are haptens or antigens and are relatively small, e.g. <10,000 daltons, such as <5,000 daltons or <2,000 daltons. Typical anti-Ans are antigen specific antibodies. Typical analytes are haptens or antigens.

There are several kinds of non-competitive assays. Sandwich assays are one of the most popular.

One kind of non-competitive receptor-ligand assays are sandwich assay. In these variants an analyte is tethered between two reactants which each is an affinity counterpart to the analyte (anti-An). Typical analytes are relatively large with molecular weights >2,000 daltons, such as >5,000 daltons >10,000 daltons, and are antigens including also immunoglobulins and antigen-specific antibodies. Typical anti-Ans are anti-An antibodies and other affinity reactants that are affinity counterparts to the analyte at issue. If, for instance, the analyte is an antigen specific antibody then one or both of the anti-Ans may be an antigen analogue while the remaining anti-An, if any, is an anti-An antibody directed towards the Fc part of the analyte. In heterogeneous assays this means that one of the anti-Ans is in immobilized or immobilizable form while the other exhibits the detectable group.

Other kinds of non-competitive assay utilizes only one anti-An that exhibits a detectable group for which the feature to me measured changes when the reactant becomes incorporated into an affinity complex together with the analyte. Well-known examples are scintillation proximity assays (SPA).

B. Catalytic Assays

In catalytic assays a component (analyte=An) of a catalytic system is assayed. The term "catalytic system" (CS) primarily contemplates biocatalytic systems, for instance enzymatic systems that are based on enzymatically active proteins or synthetic variants thereof. The term "catalytic system" also encompasses so called coupled catalytic systems in which a single catalytic system is combined with other catalytic system and/or other reaction systems such as an antigen-antibody reaction system. Components reactants) of a catalytic system can be illustrated with catalysts, substrates, co-substrates, co-factors, co-catalysts, inhibitors, promoters, activators etc. For enzymatic systems this corresponds to enzymes, substrate, co-substrates, co-enzymes, co-factors etc.

It is important to select protocol enhancers according to invention which are not substrates for the catalytic system to be studied, e.g. casein and other enhancers having polypeptide structure should be avoided if the catalytic system is protolytic. Synthetic amphiphilic macromolecular substances or inert protein substrates as protocol enhancers may then be more appropriate choices.

Enzyme systems may be selected amongst: 1) Oxidoreductases (dehydrogenases, oxidases etc), 2) Transferases, 3) Hydrolases (esterases, carbohydrases, proteases etc), 4) Lyases, 5) Isomerases, and 6) Ligases.

A component of catalytic system may be native or may have been produced synthetically or recombinantly. The component may exhibit amino acid structure, peptide structure, such as oligo- or polypeptide structure, nucleotide structure, such as oligo- or polynucleotide structure, carbohydrate structure such as oligo- or polypeptide structure, lipid structure, steroid structure, hormone structure etc. Synthetic compounds, for instance deriving from combinatorial libraries, potentially mimicking native variants of components of catalytic systems are included.

Catalytic assays to which the present invention is applied may be homogeneous or heterogeneous. A homogeneous catalytic assay contemplates that all components of the system used are in dissolved form, except for the product that may be either in dissolved or in insoluble or immobilized form. Heterogeneous catalytic assay accordingly contemplates that one or more of the components other than the product formed are in insoluble or immobilized form.

Catalytic assays typically utilize detectable groups on the substrate and/or the product. The detectable groups may typically be selected amongst the same alternatives as for receptor-ligand assays.

C. Cell Based Assays

Cell based assays means that one of the reactants transported within the transport microconduit is a suspension of cells. The cells typically are viable and subjected to one or more agents whereupon the effect of the agents on the cells are studied, possibly by utilizing a receptor-ligand protocol or a catalytic protocol of the type well-known in the field, for instance as discussed above, or by studying cell morphology, motility, proliferation etc. See also U.S. Pat. No. 6,632,656, which is incorporated herein by reference in its entirety. The agent concerned may be of any kind including also phages, viruses and the like, temperature, time, humidity, gas pressure such as $CO_2$ and/or $O_2$ pressure, nutrients, toxins, vitamins, hormones etc. The cells may be grown outside or inside the device in the presence or absence of the agent(s) concerned before the effects are studied. After subjecting the cells to the agent(s) the cells may be killed inside the microdevice, for instance lysed or fixated, while being retained in the microdevice where various released or bound cell components then are investigated.

Typical cells may be nucleated or not nucleated, anchorage-dependent or non-anchorage dependent, primary or secondary, bacterial or non-bacterial, plant cells or animal cells etc. Numerous cell lines and cultures are available for use and they can be obtained through the American Type Culture Collection (ATCC), which is an organization that serves as an archive for living cultures and genetic materials.

Cell-based assays according to the invention also may include studying of living tissue within a microdevice. The tissue may comprise a cell. The tissue may be part or separated from an organism. The cell or tissue may be comprised in at least one organism. In certain embodiments, the organism may be, but is not limited to, an eubacteria, an archaea, an eukaryote or a virus. Thus, the following are examples of cells that may be studied using the methods and compositions of the present invention.

In certain embodiments, the organism is an eubacteria. In particular embodiments, the eubacteria may be, but is not limited to, an aquifecales; a thermotogales; a thermodesulfobacterium; a member of the thermus deinococcus group; a chloroflecales; a cyanobacteria; a firmicutes; a member of the leptospirillum group; a synergistes; a member of the chlorobium flavobacteria group; a member of the chlamydia verrucomicrobia group, including but not limited to a verrucomicrobia or a chlamydia; a planctomycetales; a flexistipes; a member of the fibrobacter group; a spirochetes; a proteobacteria, including but not limited to an alpha proteobacteria, a beta proteobacteria, a delta & epsilon proteobacteria or a gamma proteobacteria. In certain aspects, an organelle derived from eubacteria are contemplated, including a mitochondria or a chloroplast.

In further embodiments, the organism is an archaea (a.k.a. archaebacteria; e.g., a methanogens, a halophiles, a sulfolobus). In particular embodiments, the archaea may be, but is not limited to, a korarchaeota; a crenarchaeota, including but not limited to, a thermofilum, a pyrobaculum, a thermoproteus, a sulfolobus, a metallosphaera, an acidianus, a thermodiscus, a igneococcus, a thermosphaera, a desulfurococcus, a staphylothermus, a pyrolobus, a hyperthermus or a pyrodictium; or an euryarchaeota, including but not limited to a halobacteriales, methanomicrobiales, a methanobacteriales, a methanococcales, a methanopyrales, an archeoglobales, a thermoplasmales or a thermococcales.

Still further, the organism is an eukaryote (e.g., a protist, a plant, a fungi, an animal). In particular embodiments, the eukaryote may be, but is not limited to, a microsporidia, a diplomonad, an oxymonad, a retortamonad, a parabasalid, a pelobiont, an entamoebae or a mitochondrial eukaryote (e.g., an animal, a plant, a fungi, a stramenopiles).

In further embodiments, the mitochondrial eukaryote may be, but is not limited to, a metazoa (e.g., an animal), a myxozoa, a choanoflagellate, a fungi (e.g., a mushroom, a mold, a yeast, a chytrid), a green plant (e.g., a green algae, a land plant), a cryptomonad, an ancyromona, plasmodiophorid, a rhodophyta, a centrohelid heliozoa, a cyanophorid, an alveolate (e.g., a dinoflagellate, a sporozoan, a ciliate), a stramenopile (e.g., a brown algae, a diatoms, an oomycete, a chrysophyte), an acantharea, a vampyrellid, a thaumatomonad, a telonema, a sticholonche, a spongomonad, a ramicristate, a pseudospora, a pseudodendromonad, a phalansterium, a phaeodarean radiolaria, a paramyxea, a luffisphaera, a leucodictyon, a kathablepharid, a histiona, a haptophyte, an ebriid, a discocelis, a diphylleia, a eesmothoracid, a cryothecomona, a copromyxid, a chlorarachnion, a cercomonad, a caecitellus, an apusomonad, an actinophryid or an acanthamoebae.

In particular aspects, the eukaryote is a metazoa (e.g., an animal). In certain aspects, the metazoa may be, but is not limited to, a porifera (e.g., a sponge), a cnidaria (e.g., a jellyfish, an anemone, a coral), a ctenophora (e.g., a comb jelly), an arthropoda (e.g., an insect, a spider, a crab), an annelida (e.g., a segmented worm), a pogonophora, a vestimentifera, an echiura, a mollusca (e.g., a snail, a clam, a squid), a sipuncula, a nemertea (e.g., a ribbon worm), a platyhelminthes (e.g., a flatworm), a chordata (e.g., a vertebrate), a hemichordata, a lophosphorates, a chaetognatha, an echinodermata (e.g., a starfish, a urchin, a sea cucumber), a pseudocoelomates, a placozoa, a monoblastozoa, rhomobozoa, an orthonectida. In particular facets the vertebrate may be a terrestrial vertebrate (e.g., a frog, a salamander, a caecilian, a reptile, a mammal, a bird) or a non terrestrial vertebrate (e.g., a sharks, a ray, a sawfish, a chimera, a ray finned fish, a lobe finned fish). In additional facets, the mammal may be a monotremata (e.g., a platypus, an echidna), a multituberculata, a marsupialia (e.g., an opossum, a kangaroo), a palaeoryctoids or an eutheria (e.g., a placental mammal).

In particular facets the eutheria may be, but is not limited to, an edentata (e.g., an anteater, a sloth, an armadillo), a pholidota (e.g., a pangolin), a lagomorpha (e.g., a rabbits), a glires, a rodentia (e.g., a mouse, a rat, a squirrel, a gopher, a porcupine, a beaver), a macroscelidea (e.g., an elephant shrew), a primates (e.g., a monkey, a lemur, a gorilla, a chimp, a human), a scandentia (e.g., a tree shrew), a chiroptera (e.g., a bat), a dermoptera (e.g., a colugo, a flying lemur), an insectivora (e.g., a shrew, a mole, a hedgehog), a creodonta, a carnivora (e.g., a dog, a cat, a bear, a raccon, a weasel, a mongoose, a hyena), a condylarthra, an artiodactyla (e.g., a pig, a deer, a cattle, a goat, a sheep, a hippopotamus, a camel), a cetacea (e.g., a whale, a dolphin, a porpoise), a tubulidentata (e.g., an aardvark), a perissodactyla (e.g., a horse, a tapir, a rhinoceros), a hyracoidea (e.g., a hyrax, a dassy), a sirenia (e.g., a manatee, a dugong, a sea cow), a desmostylia, an embrythopoda, or a proboscidea (e.g., an elephant).

In particular embodiments, eukaryote is a fungi. A fungi may be, but is not limited to, a chytridiomycota (e.g., a water mold, an allomyces), a zygomycota (e.g., a bread mold, a rhizopus, a mucor), a basidiomycota (e.g., a mushroom, a rust, a smut) or an ascomycota (e.g., a sac fungi, a yeast, a penicillium).

In certain embodiments, the eukaryote is a green plant. A green plant may be, but is not limited to, a prasinophytes, a chlorophyceae, a trebouxiophyceae, a ulvophyceae, a chlorokybales, a klebsormidiales, a zygnematales, a streptophyta, a charales, a coleochaetales or an embryophytes (e.g., a land plant). In particular facets, the embryophytes may be, but is not limited to, a marchantiomorpha (e.g., a liverwort), an Anthoceromorpha (e.g., a hornwort), a bryopsida (e.g., a moss), a lycopsida (e.g., a lycophyte), an equisetopsida (e.g., a horsetail, a sphenophyte), a filicopsida (e.g., a fern), a spermatopsida (e.g., a seed plant: a flowering plant, a conifer). In particular aspects, the spermatopsida may be, but is not limited to an angiosperm. An angiosperm may include, but is not limited to, a ceratophyllaceae, a nymphaeales, a piperales, an aristolochiales, a monocotyledons, an eudicots, a laurales, a chloranthaceae, a winterales or a magnoliales.

In certain embodiments the organism may be a virus. In particular aspects, the virus may be, but is not limited to, a DNA Virus, including but not limited to a ssDNA virus or a dsDNA virus; a DNA RNA rev transcribing virus; a RNA virus, including but not limited to a dsRNA virus, including but not limited to –ve stranded ssRNA or a +ve stranded ssRNA; or an unassigned virus.

VII. Detectable Groups

The detectable group is either natively present in a detectable reactant or has been introduced by man as a label onto a reactant. In the former case the detectable group is part of the native structure of a reactant, such as a protein, a polysaccharide, a nucleic acid etc. Typical examples are: class, subclass and species specific (IgFc) determinants in immunoglobulins/antibodies. If the label is introduced by man the final reactant is called "conjugate". Conjugates may be obtained by recombinant techniques and/or synthetically by using organic synthetic coupling chemistry.

Another categorization of detectable groups is in affinity detectable groups and signal-generating groups. Affinity detectable groups require an extra reactant that comprises an affinity counterpart to the detectable group and a second detectable group. This extra reactant is typically in the form of a man-designed conjugate. Typical affinity detectable groups are members of affinity pairs such as biotin and biotin-binding compounds such as anti-biotin antibodies, avidin, streptavidin, neutravidin etc, complementary nucleic acids, haptens and anti-hapten antibodies, lectins and carbohydrates, IgFc determinants and IgFc binding polypeptides etc. Typical signal-generating groups are particles, metals, chromophors, fluorophors (including fluorogens), radioactive groups, luminophors (including chemi- and bio luminophors), catalytically active groups such as catalysts, substrate, co-substrate, cocatalysts etc. The most popular catalytically active groups are the enzymatically active groups such as enzymes, coenzymes, cofactors, substrates, co-substrates etc.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effects on a hIL-8 Assay

The inventors have found that the performance of the sandwich assay outlined in WO 04083108 and WO 04083109 (Gyros AB) is poor with respect to detection limit, response level etc for certain serum analytes such as human interleukin 8 (hIL-8). Improvements were obtained by pre-diluting the samples in buffers containing β-casein, bovine serum albumin and NaCl.

Five samples that showed low response levels, low concentrations, and high CV between replicates were diluted in a buffer (pH about 7.4) containing 0.5% β-casein, 0.5% bovine serum albumin and 0.5 M NaCl. The dilutions (sample/buffer) were 1/15; 1/7; 1/3, 1/1 and undiluted. The response levels were drastically increased 30-100 times compared to the undiluted sample. The graphs (2-6) for the samples were parallel with the graph (1) for the standard. See FIG. 1 where the highest concentration for each sample represents the undiluted sample.

Example 2

Effects on a Human Insulin Assay

Materials and Methods
Diluents and Other Liquids:
  PBS-Tween: 15 μl Tween 20 10%+14.985 ml PBS (1×). Diluent for capture antibody and liquid for column wash in microfluidic device (CD)
  PBS-BSA: 1 ml BSA 10%+9 ml PBS (1×). Diluent for detection Ab.
  Stock inventive diluent: 1% BSA, 0.2% β-casein (SIGMA C-6905-1G, milk, min 90% purity), 1 M NaCl in PBS
  Inventive diluent for samples and standards: 0.5% BSA, 0.1% β-casein, 0.5 M NaCl in PBS 5 ml of stock diluent+5 ml MQ water.
  Alternative diluent for standards: Serum sample from a healthy fasting person. Healthy fasting persons have 2-25 μU/ml of insulin naturally, with a mean value of 9 μU/ml (Mercodia Insulin ELISA, Uppsala, Sweden).
Antibodies and Analytes:
  B-1125 Capture Ab: Anti human insulin MAb (rat IgG1; Research Diagnostic). Stock conc. 1.64 mg/ml. Assay conc. 0.1 mg/ml
  F-1203 Detection Ab: Anti human insulin MAb (rat IgG1; Research Diagnostic). Stock conc. 1000 nM. Assay conc. 25 nM
  B-1108 Capture Ab in assay for heterophilic Ab: Anti mIFNγ MAb (rat IgG1). Stock conc. 0.5 mg/ml. Assay conc. 0.1 mg/ml
  R-1614 Recombinant human insulin (Fitzgerald). Stock conc. 14.5 μU/ml. Standard curve 1-1000 μU/ml. Mw=5808 g/mol pI=5.2. High hydrophobicity. 1 μU/ml=6.95 pM=40.3 pg/ml
Samples: 13 human serum samples with insulin levels from 9-209 μU/ml according to RIA.
Instruments: Gyrolab Workstation LIF (Gyros AB, Uppsala, Sweden).

Assay Protocols and Microfluidic Devices:

Insulin sandwich assays and heterophilic antibody sandwich assays as outlined for sandwich in WO 04083108 and WO 04083109 (Gyros AB). Diluted samples and standards were dispensed to the microfluidic device.

Figure 2:
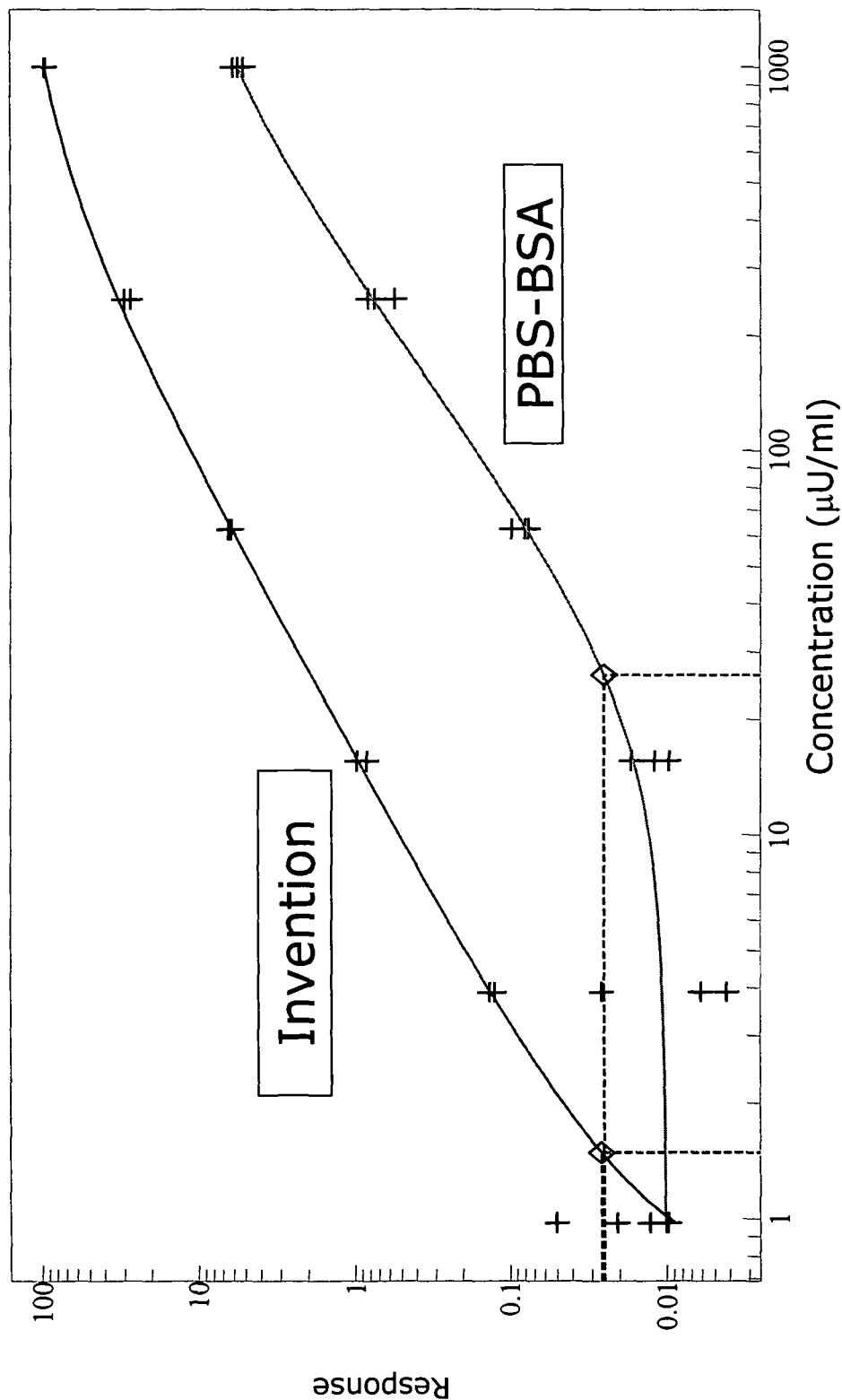
FIG. 2 illustrates a comparison between a conventional diluent and a diluent according to the invention.

A. Insulin Assays: Results of Comparison of Standard Curves for PBS-BSA and the Innovative Diluent See FIG. 2. The innovative diluent gave a much lower detection limit than the PBS-BSA diluent (0.9 µU/ml and 26 µU/ml, respectively). The dynaic range is also improved.

B. Neutralization of Heterophilic Antibodies.

Around 30-40% of all persons have heterophilic antibodies. These antibodies when present together with an analyte can interfere with immunoassays and give a false concentration of the analyte. In the assay the capture antibody (anti human insulin MAb) of the insulin assay was replaced with anti mIFNγ rat MAb (IgG1). To neutralize heterophilic antibodies, IgG was added either through a wash step or to the sample. In this experiment the IgG was added in Capture Antibody Wash Step 2. Normally PBS-Tween is used as wash solution, and in the assay all heterophilic antibodies binding to rat IgG will be measured. When adding a mixture of Bovine IgG (1.0 mg/ml) and Mouse IgG (0.2 mg/ml) the heterophilic antibodies will be reduced to a low level. The samples where analysed twice, once with PBS-Tween as wash solution and once with the IgG mixture.

It was found that the levels of heterophilic antibodies were 1-4 µU/ml, i.e. below the mean value for healthy persons. Measurable neutralization of heterophilic antibodies took place in one of the samples.

C. Dilution of Different Samples

Experiments were performed to investigate if different sample dilutions were parallel with the standard curve, i.e do we have matrix problem when the dilution factor is low? Samples with high, middle and low concentrations of insulin were diluted 1:2, 1:4, 1:8 and 1:16 in a diluent according to the invention (0.5% BSA, 0.1% β-casein and 0.5 M NaCl):

| | | |
|---|---|---|
| 1:2 | 4 µl sample | 4 µl 0.5% BSA, 0.1% β-casein and 0.5 M NaCl diluent |
| 1:4 | 4 µl 1:2 dilution | 4 µl 0.5% BSA, 0.1% β-casein and 0.5 M NaCl diluent |
| 1:8 | 4 µl 1:4 dilution | 4 µl 0.5% BSA, 0.1% β-casein and 0.5 M NaCl diluent |
| 1:16 | 4 µl 1:8 dilution | 4 µl 0.5% BSA, 0.1% β-casein and 0.5 M NaCl diluent |

The graph from dilution 1:2 to 1:16 was parallel with the standard curve for all samples, i.e. no matrix effects when diluting at least 1:2.

Example 3

Screening for Optimal Combinations of Protocol Enhancers for Analytical Protocols Assay Protocol:

Sandwich assays as outlined WO 04083108 and WO 04083109 (Gyros AB). Diluted samples and standards were dispensed to the microfluidic device.

Analytes (pI):

hIFNγ (9.64), hMCP-1 (9.39), hIL-4 (9.26), hIL-8 (9.02), hTNFβ (8.94), mIFNγ (8.8), mIL-4 (8.3), mIL-10 (8.2), hIL-2 (7.05), hIL-5 (7.05), hTNFα (7.0), mIL-6 (6.5), hIL-6 (6.25), hIL-1 (5.95), hInsulin (5.2), rInsulin, hMMP-2 (5.02), mTNFα (5.0), mIL-2 (4.9), mMIP-1β (4.77) (h=human, m=mouse, and r=rat). Concentration: 100 pM for Samples: 100 pM in analyte. Serum milieu Protocol Enhancers:

1. Amphiphilic macromolecular substance: β-casein, Pluronic F127 and F68 (BASF) (triblock copolymer $(EO)_m(PO)_n(EO)_m$ where EO is ethylene oxide and PO propylene oxide.
2. Salt: NaCl
3. Detergents: Non-ionic: Tween 20 and 80 (Merck), Triton X100 (Sigma), Pluronic F127 and F68 (BASF), Glucopone (Fluka), Brij 35 (Aldrich); b) Zwitterionic CHAPS (Sigma), Zittergent (Calbiochem), DPC (dodecylphosphocholine); c) Cationic: CTAB (Sigma).

Evaluation criteria: CV and detection level.

Result:

Representative results are concluded in FIG. 3, where 0 stands for not recommended, + for acceptable, and very acceptable. The risk for negative effects appears to be smallest for diluent 3 and 4 ("Tween" and "Pluronic", respectively), probably with some preference for diluent 4. The results for the detergents indicated that non-ionic detergents had the most general applicability.

Certain innovative aspects of the invention are defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method for the preparation of a liquid sample and transport thereof in a microfluidic device having a microfluidic transport conduit connected to a reaction microcavity, wherein the microfluidic transport conduit has an inner surface and is made from metal or plastics, the method which comprises providing a biologically derived liquid sample containing a reactant being a bioorganic compound exhibiting hydrophobic groups and/or charged groups and which is capable of interacting with the inner surface of the microfluidic transport conduit;

diluting the liquid sample with a buffer containing an amphiphilic macromolecular substance selected from caseins which is capable of attaching to the inner surface of the microfluidic transport conduit and which is not natively present in the liquid sample;

dispensing the diluted sample to the microfluidic transport conduit of the microfluidic device; and applying a driving force for transporting the sample through the microfluidic transport conduit to the reaction microcavity, wherein the amphiphilic macromolecular substance minimizes interaction between the reactant and the inner surface of the microfluidic transport conduit and thereby minimizes loss of reactant during the transport to the reaction microcavity.

2. The method of claim 1, wherein said amphiphilic macromolecular substance is capable of forming micelles in water.

3. The method of claim 1, wherein the sample comprises a serum albumin concentration in the range of about 0.001% to about 5%.

4. The method of claim 1, wherein the sample comprises a salt concentration in the range >0.10 M.

5. The method of claim 1, wherein the microfluidic transport conduit is made of metal.

6. The method of claim 1, wherein the microfluidic device has a plurality of microfluidic transport conduits.

7. The method of claim 1, wherein said microfluidic transport conduit is made from plastics.

8. The method of claim 1, wherein said sample comprises immunoglobulin.

9. The method of claim 1, wherein said reactant has a structure selected from the group consisting of peptide structure, nucleic acid structure, carbohydrate structure and lipid structure.

10. The method of claim 1, wherein said reactant is an ampholyte with a pI larger or smaller than pH of the aliquot.

* * * * *

UNITED STATES PATENT AND TRADEMARK OFFICE
CERTIFICATE OF CORRECTION

PATENT NO. : 8,592,219 B2  Page 1 of 1
APPLICATION NO. : 11/038712
DATED : November 26, 2013
INVENTOR(S) : Rickard Kange et al.

It is certified that error appears in the above-identified patent and that said Letters Patent is hereby corrected as shown below:

On the Title Page, below Item (65)

Add section

--(30) Foreign Application Priority Data

Jan. 17, 2005   (SE)                                    05001318.--.

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,592,219 B2 | Page 1 of 1 |
| APPLICATION NO. | : 11/038712 | |
| DATED | : November 26, 2013 | |
| INVENTOR(S) | : Kange et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1216 days.

Signed and Sealed this
Twenty-first Day of April, 2015

Michelle K. Lee
*Director of the United States Patent and Trademark Office*